(12) United States Patent
Perez Gomariz et al.

(10) Patent No.: US 6,429,188 B1
(45) Date of Patent: Aug. 6, 2002

(54) METHOD FOR TREATING THE ENDOTOXIC SHOCK IN MAMMALS

(75) Inventors: Rosa Maria Perez Gomariz; Javier Leceta Martinez; Mario Delgado; Carmen Martinez, all of Madrid (ES)

(73) Assignee: Universidad Complutense de Madrid, Madrid (ES)

( * ) Notice: Subject to any disclaimer, the term of this patent is extended or adjusted under 35 U.S.C. 154(b) by 0 days.

(21) Appl. No.: 09/446,352

(22) PCT Filed: Apr. 16, 1999

(86) PCT No.: PCT/ES99/00101

§ 371 (c)(1),
(2), (4) Date: Apr. 3, 2000

(87) PCT Pub. No.: WO99/53944

PCT Pub. Date: Oct. 28, 1999

(30) Foreign Application Priority Data

Apr. 17, 1998 (ES) ............................................. 9800814

(51) Int. Cl.⁷ ........................ A01N 37/18; A61K 38/00; C12P 21/02; C12P 21/04; C07K 14/00

(52) U.S. Cl. ........................... 514/2; 514/12; 435/69.5; 435/69.52; 530/300

(58) Field of Search ............................. 435/7.21, 7.24, 435/69.5, 69.52, 183; 436/501, 94; 530/300, 350; 514/2, 12

(56) References Cited

PUBLICATIONS

Itoh et al., Human preprovasoactive intestinal polypeptide contains a novel PHI–27–like peptide, PHM–27. Nature, 304–547–549, 1983.*

Nishzawa et al., Nucleotide sequence divergence and functional constraint in VIP precursor mRNA evolution between human and rat. FEBS Lett., 183, 55–59, 1985.*

Lamperti et al., Characterization of the gene and messages for vasoactive intestinal polypeptide (VIP) in rat and mouse. Brain Res. Mol. Brain Res., 9, 217–231, 1991.*

Soares et al., a vasoactive peptide maxadilan from sand fly saliva inhibits TNF–alpha and induces IL–6 by mouse macrophages through interaction with the pituitary adenylate cyclase–activating polypeptide (PACAP) receptor. J. Immunol. 160, 1811–1816, 1998.*

Delgado et al., Vasoactive intestinal peptide (VIP) and pituitary adenylate cyclase activation polypeptide (PACAP) protect mice from lethal endotoxemia through the inhibition of TNF–alpha and IL–6. J. Immunology, 162, 1200–1205, Jan. 15, 1999.*

* cited by examiner

Primary Examiner—Ethan C. Whisenant
Assistant Examiner—Frank Lu
(74) Attorney, Agent, or Firm—Notaro & Michalos P.C.

(57) ABSTRACT

Method for the treatment of endotoxic shock in mammals. The use of vasoactive intestinal peptide (VIP) and peptide activating hypofissiary adenylate cyclase (PACAP) is described in the treatment of endotoxic shock in mammals. These substances inhibit the production of tumor necrosis factor (TNF) and interleukin 6 (IL-6).

8 Claims, 6 Drawing Sheets

METHOD FOR TREATING THE ENDOTOXIC SHOCK IN MAMMALS

STATE OF THE ART

Endotoxic shock is still the main cause of death in hospital. Strategies for combating the effects of endotoxic shock are centred on counteracting the bacterial agents responsible for these effects, restoring the hemodynamic parameters, preventing cellular activation and modifying the action of the defence mechanisms (Boyd O; Current Opinion in Anaesthesiology 1996, 9:98)

It is currently accepted that the inflammatory response to bacterial products directly contributes to endotoxic shock (Parillo J E; New England Journal of Medicine 1993, 328:1471). Toxic bacterial products and those released during tissue damage activate the defence mechanisms, with implication of cells such as neutrophils, monocytes, macrophages and endothelial cells, and of mediators such as cytokines, platelet activation factor, metabolites of arachidonic acid and nitric oxide, leading to hemodynamic changes and organ lesions for the host (Moldawer L L; Critical Care Medicine 1994,22:3). Many cytokines have been proposed as markers of the seriousness of the development of septic shock, The levels of circulating TNF-, IL-1, IL-6 and IL-8 have been correlated with e probability of overcoming a septic episode. TNF-, and IL-1 administrated to humans or experimental animals reproduce many of the hemodynamic signs of septic shock (Tracey K J et al., 1986, Science 234:470). Their inhibition by injection of antagonist receptors and blocking monoclonal antibodies have been studied with a wide range of results (Fisher C J et al.; 1994, Critical Care Medicine, 22:12). Of the immunological markers the levels of circulating IL-6 are the best indicators of the seriousness of the sepsis and the possibilities of overcoming the episode (Liaw Y S et al; 1997, Journal of the Formosan Medical Association, 96:685). Despite the advances in knowledge of the mechanisms and of the technical and pharmacological progress there are still few results in terms of an improvement in the data for mortality rate. This rate corresponds to 200,000 deaths per year in the United States and Europe (Vicent J-L and Chamlou R; Current Opinion in Anaesthesiology 1996, 9:146).

The Vasoactive Intestinal Peptide (VIP) is a basic peptide of 28 amino acid units whose sequence is (Mutt V and Said S I; European Biochemistry 1974, 42:581):

His-Ser-Asp-Ala-Val-Phe-Thr-Asp-Asn-Tyr-Thr-Arg-Leu-Arg-Lys-Met-Ala-Val-Lys-Lys-Tyr-Leu-Asn-Ser-Ile-Leu-Asn-NH2, (SEQ ID NO;1)

It was initially isolated from the small intestine of pig and later identified in the brain and terminals of the peripheral nervous system. It was established to be a neuropeptide with neuromodulating properties (Fahrenkrug J; Pharmacology and Toxicology J. 1993, 72:354). Its name is derived from its peripheral vasodilatory properties. VIP has also been identified in rat mast cells and in granulomas (Cutz E. et al.; Nature 1978, 275:661). Immunological studies carried out on histologic sections of thymus, spleen and lymphatic ganglia from rats have identified immunoactive VIP in the lymphocytes of these organs (Leceta et al. Advances in Neuroimmunology 1996, 6:29). VIP exercises its biological effects through membrane receptors belonging to the super family of seven hydrophobic domains coupled to G proteins, which transduce information to the end effector molecules (Laburthe M y Couvineau A; Annals of the New York Academy of Sciences 1988, 527:296). Receptors for VIP have been characterised in several tissues such as liver and adipose tissue among others. These correspond to two types, the so-called VIP1-R (Ishihara T et al.; Neuron 1992, 8:811) and VIP2-R (Lutz E. et al. FEBS Letters 1993, 334:3). In the immune system specific receptors have been characterised for VIP in a variety of immune cells which include human peripheral lymphocytes, human monocytes, rat and mouse lymphocytes, rat alveolar macrophages and peritoneal macrophages of rat and mouse (Delgado M et al.; Regulatory Peptides 1996, 62:161). VIP modulates a great variety of immune functions such as phagocyte function, at every stage of the process, the proliferative response, production of immunoglobin, NK activity and cytokine production (Ganea et al.; Advances in Neuroimmunology 1996, 6:61).

The pituitary adenylate cyclase-activating polypeptide (PACAP) is a member of the family of peptides of secretin/VIP/glucagon, of which two molecular forms are known, namely PACAP-38 AND PACAP-27, whose sequences are as indicated (Ogi K et al., Biochemical and Biophysical Research Communication 1993, 196:1511): PACAP-38

His-Ser-Asp-Gly-Ile-Phe-Thr-Asp-Ser-Tyr-Ser-Arg-Tyr-Arg-Lys-Gln-Met-Ala-Val-Lys-Lys-Thr-Leu-Ala-Ala-Val-Leu-Gly-Lys-Arg-Tyr-Lys-Arg-Tyr-Lys-Gln-Arg-Val-Lys-Asn-Lys-NH2, (SEQ ID NO:2)

PACAP-27

His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-NH2, (SEQ ID NO:3)

Both peptides are widely distributed in the central and peripheral nervous system. There are also PACAP producing cells in lung, pancreatic B cells and intestine (Arimura A; Regulatory Peptides 1992, 37:287). In the immune system a large abundance of PACAP positive cells have been described in central and peripheral lymphoid organs (Gaytan F et al.; Cell and Tissue Research 1994, 276:233). For PACAP three types of receptor have been described (Shivers B D et al,; Endocrinology 1991, 128:3055; Inagaki N y col.; Proceedings of the National Academy of Sciences USA 1994, 91:2679): the PACP type I receptor (PACAP-R-I) with equal affinity for PACAP-38 and PACAP-27, but which has an affinity 300 to 1000 times less for VIP; the PACAP type II receptor (PACAP-R-II) which recognises with the same affinity VIP, PACAP-38 and PACAP-27 and is thus denominated the common receptor of VIP-PACAP and corresponds to the receptor VIP VIP1-R, and the PACAP type III receptor (PACAP-R-III) which corresponds to the receptor VIP VIP2-R. Up until present there have been few studies on the biological actions of PACAP on the immune system. The effects of PACAP are often similar to those of VIP mnodulating the phagocyte function and proliferative responses.

DESCRIPTION OF THE INVENTION

The object of this invention is to develop preparation of VIP, PACAP and analogues thereof as therapeutic agents in the treatment of endotoxic shock.

The treatment consists of the administration to mammals in need thereof, of an effective quantity of an agent that inhibits the production of tumor necrosis factor (TNF) in an acceptable pharmaceutical vehicle.

VIP and PACAP have anti-inflammatory effects and inhibit the production of IL-1, IL-6 and TNF-, in animal models of the induction of endotoxic shock. As these cytokines play an important role in the development of said syndrome, VIP and PACAP can be used to regulate their production.

It is known that most of the effects of the endotoxic shock are mediated by activation of the immune system and the inflammatory mechanisms of the host as response to bacterial products. Macrophages play a key role in this process as after their activation factors such as nitric oxide, prostaglandins and cytokines responsible for symptoms such as fever, hypotension, disseminated micro-coagulation, multiple organ failure and finally death, are produced. Similarly, high levels of circulating TNF, IL-1 and IL-6 associated with endotoxemia have been described. In animal models these symptoms are reproduced both by administration of bacterial endotoxins (LPS) and by injection of TNF and IL-1. Other studies have underlined the diagnostic value in terms of the probability of survival represented by the levels of circulating IL-6.

The tumor necrosis factor (TNF) is produced by several types of cell that include monocytes and macrophages, T and B lymphocytes, neutrophils, mast cells, tumorous cells and fibroblasts. It is an important regulatory factor in other pro-inflammatory cytokines, such as IL-1β, IL-6 and IL-8. TNFα induces the expression of adhesion molecules in endothelial cells, activates leukocytes to destroy the microorganisms, acts on the hepatocytes to increase the synthesis of serum proteins which contribute to the acute phase response and activate the coagulation system. Overproduction thereof leads to immunopathologic diseases, autoimmunity and inflammation.

IL-6 is a multi-functional cytokine produced both by lymphocytes and by non-lymphoid cells. It regulates several aspects of the immune response, such as the production of proteins that mediate acute phase and hematopoiesis. Furthermore, it acts as a mediator in inflammatory response. Its production is regulated by several factors, which include TNFα, IL-1 and bacterial endotoxin (LPS).

Strategies of neutralisation of these cytokines have been tested in the treatment of endotoxic shock but the results do not indicate that there is a greater long-term survival. A treatment that inhibits the production of TNF and, IL-6 would represent a considerable improvement in the evolution of endotoxic shock and in the probabilities of survival. Administration of VIP and PACAP in animal models achieves these effects and our invention consists of using a treatment with these neuropeptides for increasing the survival in cases of endotoxic shock.

EMBODIMENT OF THE INVENTION

The examples that follow are only to illustrate the results obtained and do not limit the use of the invention. This use is laid out in detail in the specified claims.

EXAMPLE 1

VIP and PACAP Inhibit the Production of TNFα in Macrophages Stimulated with LPS

Figure 1:
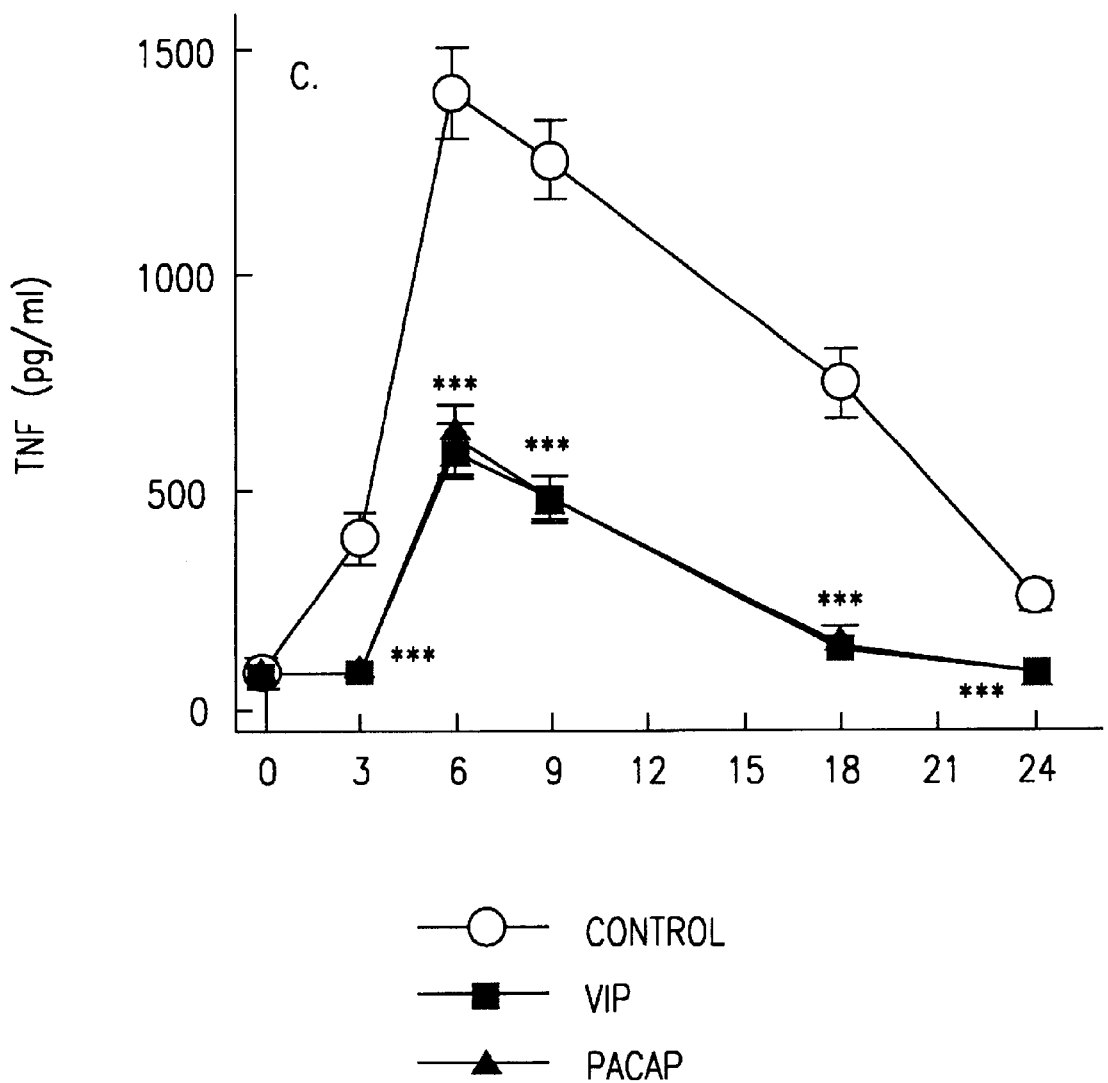
FIG. 1 represents the production of TNFα by murin macrophages in culture (5×10$^5$ cells/nil) stimulated with 10 ngr/ml of LPS in presence or absence of 10$^{-8}$ M of VIP or PACAP over a period of 24 hours.
Figure 2:
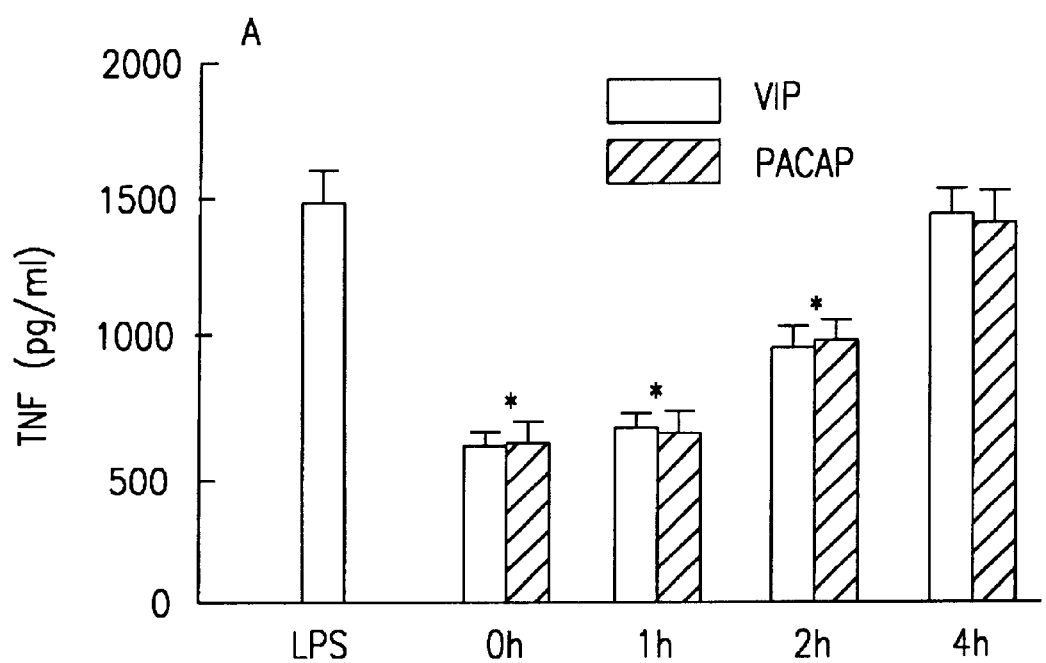
FIG. 2 represents the production of TNFα by murin macrophages in culture (5×10$^5$ cells/ml) after 6 hours of culture with 10 ngr/ml of LPS and to which 10$^{-8}$ M of VIP or PACAP is added at different times.

In experiments carried out in vitro VIP and PACAP inhibit the production of TNFα in peritoneal murin macrophages stimulated with LPS. The highest degree of inhibition reaches levels near to 60% and occurs with doses of stimulation between 1 and 10 ng/ml of LPS. The $IC_{50}$ is around 80 pM, both for VIP and for PACAP and the effect was observed until the end of the experiment (see FIG. 1). The inhibitory effect is the same if both neuropeptides are added up until 1 hour after stimulating the macrophages with LPS, although it reduces progressively until disappearing if added after 4 hours (see FIG. 2).

EXAMPLE 2

VIP and PACAP Reduce the Levels of Circulating TNFα After Injection with LPS

In an experiment carried out with mice the levels of circulating TNFα 2 hours after injection of 25 μgr. of LPS approach 4 ngr./ml. Simultaneous administration of 5 nmol of VIP or PACAP reduced said levels by 60%.

EXAMPLE 3

VIP and PACAP Inhibit the Production of IL-6 in Macrophages Stimulated with LPS

Figure 3:
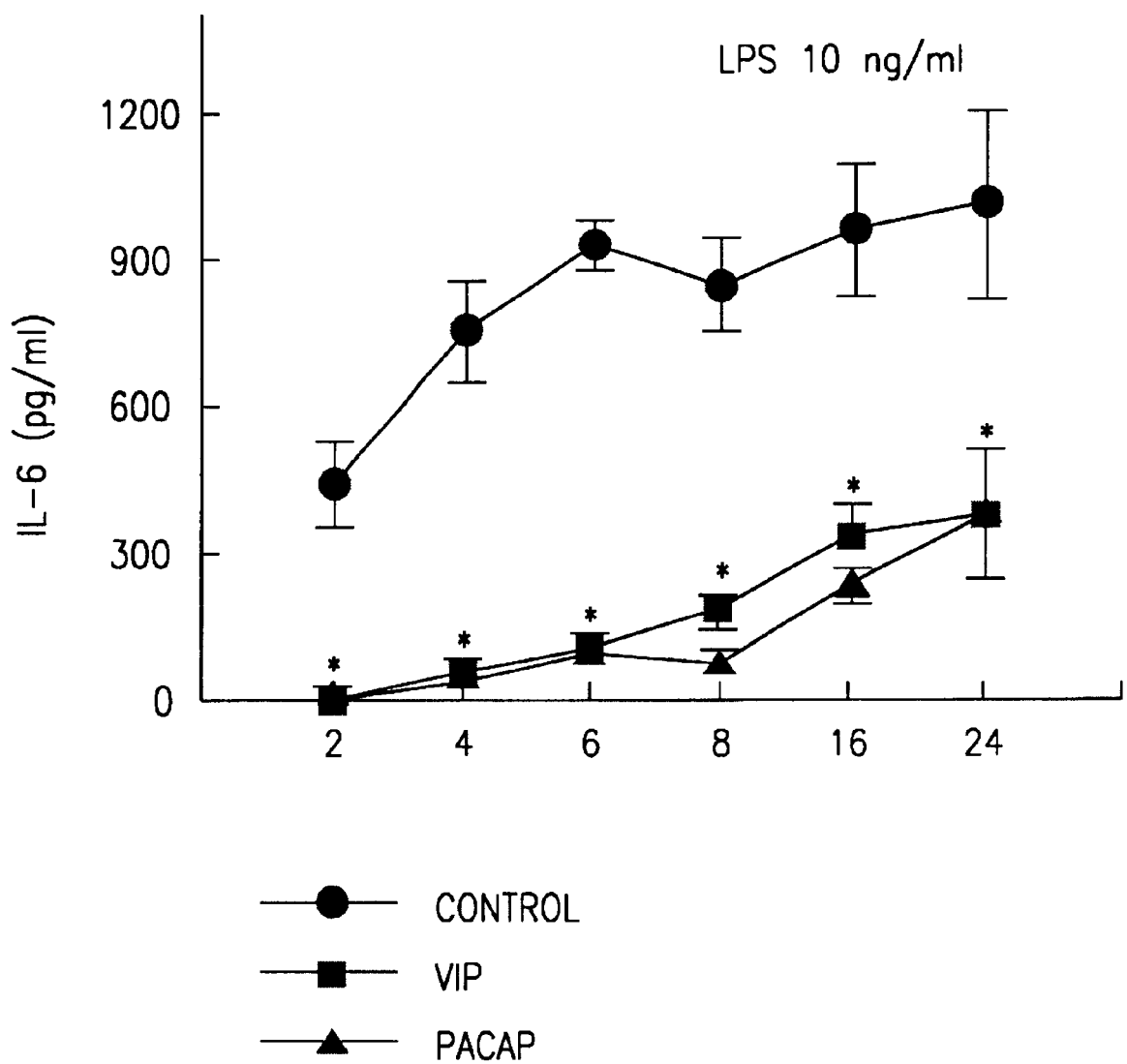
FIG. 3 represents the production of IL-6 by murin macrophages in culture (5×10$^5$ cells/ml) stimulated with 10 ngr/ml of LPS in presence or absence of 10$^{-8}$ M of VIP or PACAP over a period of 24 hours.
Figure 4:
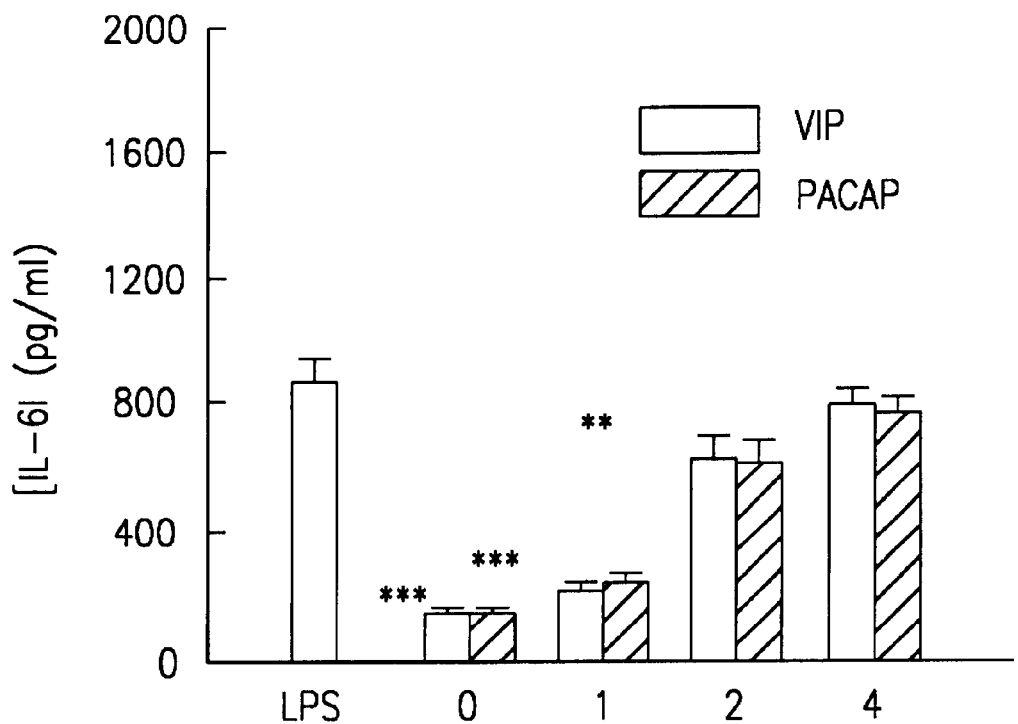
FIG. 4 represents the production of IL-6 by murin macrophages in culture (5×10$^5$ cells/ml) after 6 hours of culture with 10 ngr/ml of LPS and to which 10$^{-8}$ M of VIP or PACAP is added at different times.

In experiments carried out in vitro VIP and PACAP inhibit the production of IL-6 in peritoneal murin macrophages stimulated with LPS. The highest degree of inhibition reaches levels near to 90% and occurs with doses of stimulation of 10 ngr./ml of LPS. The $IC_{50}$ is 8.6 pM, both for VIP and for PACAP and the effect was observed until the end of the experiment (see FIG. 3). The effect is also observed if the neuropeptides are added after stimulation with LPS, although the degree of inhibition is progressively less (see FIG. 4).

EXAMPLE 4

VIP and PACAP Reduce the Levels of Circulating IL-6 After Injection with LPS

In an experiment carried out with mice the levels of circulating IL-6 2 hours after injection of 25 μgr. of LPS approach 1.5 ngr./ml Simultaneous administration of 5 nmol of VIP or PACAP reduced said levels by 60% and 75% respectively.

EXAMPLE 5

Figure 5:
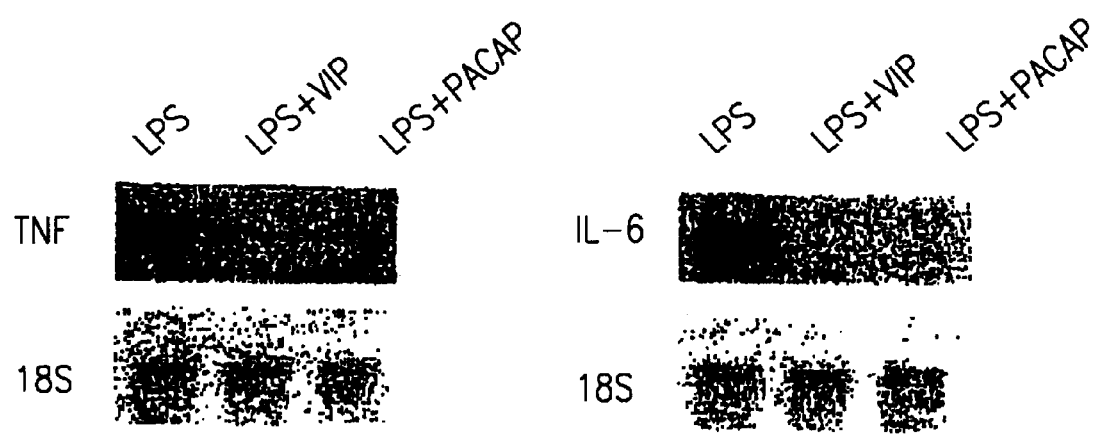
FIG. 5 shows the Northern blot analysis for the presence of mRNA corresponding to TNFα and IL-6 in macrophages stimulated with LPS in presence or absence of VIP or PACAP (18S represents the corresponding rRNA as a control of the total amount of RNA load).

VIP and PACAP Regulate the Production of TNFα and IL-6 at a Transcriptional Level Mouse macrophages were submitted to the experimental conditions of examples 1 and 3 and their mRNA isolated. This was then analysed using the Northern Blot technique to detect mRNA of TNFα and IL-6. FIG. 5 shows the absence of transcripts for TNFα or IL-6 when the macrophages activated with LPS are also exposed to VIP or PACAP.

EXAMPLE 6

VIP and PACAP Protect Against the Lethal Effects of LPS

Figure 6:
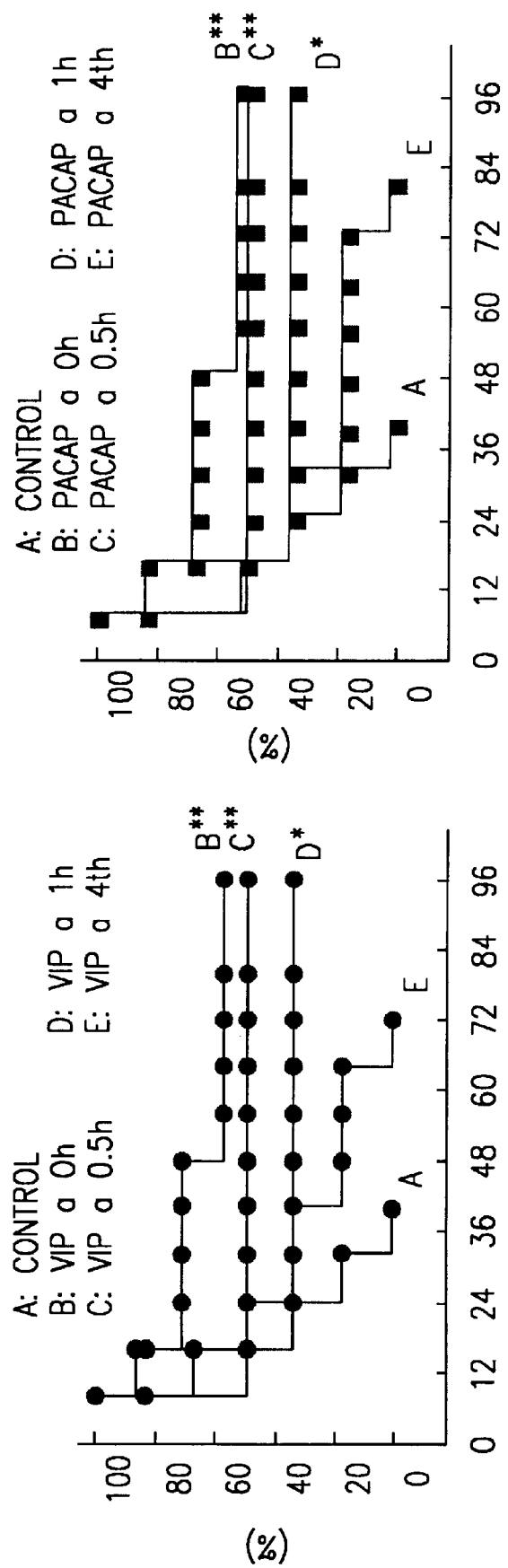
FIG. 6 represents the survival of mice injected with 400 μgr. of LPS and, either simultaneously or after 30 minutes, 1 or 4 hours, with 5 nmol. of VIP or PACAP. A. Control; B: VIP a 0 h.; C: VIP a 0.5 h; D: VIP a 1 h.; E: VIP a 4 h.

An experiment was carried out in which the survival over a 4-day period was studied of mice that had been injected with 400 μgr. of LPS. The results are shown in FIG. 6. The mortality in these circumstances was 100% after 36 hours. With simultaneous administration of 5 nmol. of VIP or PACAP a survival rate of 60% was attained at the end of the experiment. Administration of neuropeptides up to 1 hour after injection with LPS still gave survival rates near to 50%.

2. The method of claim 1 wherein the agent is the vasoactive intestinal peptide (VIP) SEQ ID NO:1.

3. The method of claim 1 wherein the agent is the pituitary adenylate cyclase-activating polypeptide (PACAP) SEQ ID NO:2.

4. The method of claim 1 wherein the agent is the pituitary adenylate cyclase-activating polypeptide (PACAP) SEQ ID NO:3.

5. A method for the treatment of endotoxic shock in mammals which comprises administering to said mammals an effective amount of an agent that inhibits the production of interleukin 6 (IL-6) said agent being selected from the group consisting of SEQ ID NO:1, SEQ ID NO:2 and SEQ ID NO:3, in a pharmaceutically acceptable vehicle.

6. The method of claim 5 wherein the agent is the vasoactive intestinal peptide (VIP) SEQ ID NO:1.

We claim:

1. A method for the treatment of endotoxic shock in mammals which comprises administering to said mammals an effective amount of an agent that inhibits the production of tumor necrosis factor (TNF), said agent being selected from the group consisting of SEQ ID NO:1, SEQ ID NO:2 and SEQ ID NO:3, in a pharmaceutically acceptable vehicle.

7. The method of claim 5 wherein the agent is the pituitary adenylate cyclase-activating polypeptide (PACAP) SEQ ID NO:2.

8. The method of claim 5 wherein the agent is the pituitary adenylate cyclase-activating polypeptide (PACAP) SEQ ID NO:3.

* * * * *

SEQUENCE LISTING

<160> NUMBER OF SEQ ID NOS: 3

<210> SEQ ID NO 1
<211> LENGTH: 28
<212> TYPE: PRT
<213> ORGANISM: Isolated from small intestines and brains of pigs

<400> SEQUENCE: 1

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 2
<211> LENGTH: 38
<212> TYPE: PRT
<213> ORGANISM: Isolated from ovine hypothalmi or rat brains

<400> SEQUENCE: 2

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 3
<211> LENGTH: 27
<212> TYPE: PRT
<213> ORGANISM: Isolated from ovine hypothalmi or rat brains

<400> SEQUENCE: 3

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25